US009487825B2

(12) United States Patent
Sachidanandam et al.

(10) Patent No.: US 9,487,825 B2
(45) Date of Patent: Nov. 8, 2016

(54) POOLED ADAPTER STRATEGY FOR REDUCING BIAS IN SMALL RNA CHARACTERIZATION

(75) Inventors: Ravi Sachidanandam, Brooklyn, NY (US); Anitha Jayaprakash, New York, NY (US); Brian Brown, Mew York, NY (US)

(73) Assignee: MOUNT SINAI SCHOOL OF MEDICINE, New York, NY (US)

( * ) Notice: Subject to any disclaimer, the term of this patent is extended or adjusted under 35 U.S.C. 154(b) by 0 days.

(21) Appl. No.: 13/470,872

(22) Filed: May 14, 2012

(65) Prior Publication Data
US 2012/0322691 A1 Dec. 20, 2012

Related U.S. Application Data

(60) Provisional application No. 61/486,214, filed on May 13, 2011.

(51) Int. Cl.
*C12Q 1/68* (2006.01)
(52) U.S. Cl.
CPC .......... *C12Q 1/6855* (2013.01); *C12N 2320/10* (2013.01)
(58) Field of Classification Search
None
See application file for complete search history.

(56) References Cited

U.S. PATENT DOCUMENTS

| 5,629,179 A * | 5/1997 | Mierendorf ........ C12N 15/1096 435/91.2 |
| 6,194,454 B1 * | 2/2001 | Dow .............................. 514/522 |
| 7,323,305 B2 * | 1/2008 | Leamon ............ B01L 3/502707 435/175 |
| 2009/0004665 A1 * | 1/2009 | Brenner ................ C12Q 1/6827 435/6.16 |
| 2009/0105959 A1 * | 4/2009 | Braverman ............... C12Q 1/68 702/19 |
| 2009/0170713 A1 * | 7/2009 | van Eijk ............... C12Q 1/6858 506/7 |
| 2009/0233802 A1 * | 9/2009 | Bignell ................ C12Q 1/6874 506/2 |
| 2011/0104785 A1 * | 5/2011 | Vaidyanathan ........ C12N 15/10 435/196 |
| 2012/0028814 A1 * | 2/2012 | Toloue ................. C12Q 1/6869 506/2 |

FOREIGN PATENT DOCUMENTS

WO 2008/150377 12/2008
WO WO 2008/150377 A1 * 12/2008

OTHER PUBLICATIONS

Hafner et al., "Identification of microRNAs and other small regulatory RNAs using cDNA library sequencing", Methods, vol. 44, p. 3-12 (2008).*
Shekhtman et al. (Optimization of Transrenal DNA Analysis: Detection of Fetal DNA in Maternal Urine, Clin Chem. Apr. 2009;55(4):723-9. Epub Jan. 30, 2009).*
Starega-Roslan et al. (Structural basis of microRNA length variety, Nucleic Acids Res. Jan. 2011; 39(1): 257-268. Published online Aug. 25, 2010).*
Wang et al. (CLIP: Construction of cDNA libraries for high-throughput sequencing from RNAs cross-linked to proteins in vivo, Methods. Jul. 2009;48(3):287-93. Epub Mar. 9, 2009).*
Craig et al. (Identification of genetic variants using bar-coded multiplexed sequencing, Nat Methods. Oct. 2008;5(10):887-93. Epub Sep. 14, 2008).*
Meyer et al. (Targeted high-throughput sequencing of tagged nucleic acid samples, Nucleic Acids Res. 2007;35(15):e97. Epub Aug. 1, 2007).*
Meyer et al. (Parallel tagged sequencing on the 454 platform, Nat Protoc. 2008;3(2):267-78, Published online: Jan. 31, 2008).*
Wang et al. (CLIP: construction of cDNA libraries for high-throughput sequencing from RNAs cross-linked to proteins in vivo, Methods. Jul. 2009;48(3):287-93. doi: 10.1016/j.ymeth.2009.02. 021. Epub Mar. 9, 2009).*
Lennon et al. (A scalable, fully automated process for construction of sequence-ready barcoded libraries for 454, Genome Biol. 2010; 11(2): R15. Published online Feb. 5, 2010).*
Parameswaran et al. (A pyrosequencing-tailored nucleotide barcode design unveils opportunities for large-scale sample multiplexing, Nucleic Acids Res. 2007;35(19):e130. Epub Oct. 11, 2007).*
Amitsur et al. "Bacteriophage t4 anticodon nuclease, polynucleotide kinase and RNA ligase reprocess the host lysine tRNA" The EMBO Journal 6, 8 (Aug. 1987), 2499-2503. PMID: 2444436.
Aravin et al. The Piwi-piRNA pathway provides an adaptive defense in the transposon arms race. Science (New York, N.Y.) 318, 5851 (Nov. 2007), 761-764. PMID:17975059.
Baccarini et al. "Kinetic analysis reveals the fate of a MicroRNA following target regulation in mammalian cells" Current Biology: CB 21, 5 (Mar. 2011), 369-376. PMID:21353554.
Baker "MicroRNA profiling: separating signal from noise" Nat Meth 7, 9 (2010), 687-692.
Berezikov et al. "Approaches to microRNA discovery" Nature Genetics 38 Suppl (Jun. 2006), S2-7. PMID: 16736019.
Berezikov et al. "Diversity of microRNAs in human and chimpanzee brain" Nature Genetics 38, 12 (Dec. 2006), 1375-1377. PMID:17072315.

(Continued)

Primary Examiner — Aaron Priest

(57) ABSTRACT

Modified nucleic acid adapters are provided that collectively provide a mixture of nucleotides at the 3' end of 5' adapters and at the 5' end of 3' adapters such that at least one adapter in each set has any given nucleotide at position 1, i.e., the nucleotide position available for ligation to a small RNA, and has any given nucleotide at position 2 adjacent to position 1 for use in overcoming bias during nucleic acid manipulation, such as small RNA characterization and/or profiling by, e.g., deep sequencing, along with methods for use of the modified adapters in small RNA characterization. The modified adapters have at least two mixed nucleotides at the adapter terminus to be ligated to a nucleic acid such as a small RNA.

17 Claims, 10 Drawing Sheets

(56) References Cited

OTHER PUBLICATIONS

Brennecke et al. "Discrete small RNA-generating loci as master regulators of transposon activity in *Drosophila*" Cell 128, 6 (Mar. 2007), 1089-1103. PMID: 17346786.

Brown et al. "Endogenous microRNA can be broadly exploited to regulate transgene expression according to tissue, lineage and differentiation state" Nature Biotechnology 25, 12 (Dec. 2007), 1457-1467. PMID:18026085.

Cerutti, H., and Casas-Mollano, J. A. On the origin and functions of RNA-mediated silencing: from protists to man. Current Genetics 50, 2 (Aug. 2006), 81-99. PMID: 16691418.

Chen et al. "Real-time quantification of microRNAs by stem-loop RT-PCR" Nucleic Acids Research 33, 20 (2005), e179. PMID: 16314309.

Chiang et al. "Mammalian microRNAs: experimental evaluation of novel and previously annotated genes" Genes & Development 24, 10 (May 2010), 992-1009. PMID: 20413612.

Czech et al. "An endogenous small interfering RNA pathway in *Drosophila*" Nature 453, 7196 (Junv ce 2008), 798-802. PMID:18463631.

Elbashir et al. "RNA interference is mediated by 21- and 22-nucleotide RNAs" Genes & Development 15, 2 (Jan. 2001), 188-200. PMID: 11157775.

Farazi et al. "miRNAs in human cancer" The Journal of Pathology 223, 2 (Jan. 2011), 102-115. PMID: 21125669.

Git et al. "Systematic comparison of microarray profiling, real-time PCR, and next-generation sequencing technologies for measuring differential microRNA expression" RNA (New York, N.Y.) 16, 5 (May 2010), 991-1006. PMID:20360395.

Goff et al. Ago2 immunoprecipitation identifies predicted microRNAs in human embryonic stem cells and neural precursors. PloS One 4, 9 (2009), e7192. PMID: 19784364.

Goff et al. "Rational probe optimization and enhanced detection strategy for microRNAs using microarrays" RNA Biology 2, 3 (Sep. 2005), 93-100. PMID:17114923.

Hafner et al. Identification of microRNAs and other small regulatory RNAs using cDNA library sequencing. Methods (San Diego, Calif.) 44, 1 (Jan. 2008), 3-12. PMID: 18158127.

Jeffrey "Cancer biomarker profiling with microRNAs" Nature Biotechnology 26, 4 (Apr. 2008), 400-401. PMID:18392022.

Jones et al. "Zcchc11-dependent uridylation of microRNA directs cytokine expression" Nature cell biology 11, 9 (Sep. 2009), 1157-1163. PMID: 19701194 PMCID:2759306.

Kozomara et al. miRBase: integrating microRNA annotation and deep-sequencing data. Nucleic Acids Research 39, Database issue (Jan. 2011), D152-157. PMID: 21037258.

Kuchenbauer et al. In-depth characterization of the microRNA transcriptome in a leukemia progression model. Genome Research 18, 11 (Nov. 2008), 1787-1797. PMID: 18849523.

Landgraf et al. "A mammalian microRNA expression atlas based on small RNA library sequencing" Cell 129, 7 (Jun. 2007), 1401-1414. PMID: 17604727.

Lau et al. "An abundant class of tiny RNAs with probable regulatory roles in caenorhabditis elegans" Science (New York, N.Y.) 294, 5543 (Oct. 2001), 858-862. PMID: 11679671.

Lee et al. Complexity of the microRNA repertoire revealed by next-generation sequencing. RNA (New York, N.Y.) 16, 11 (Nov. 2010), 2170-2180. PMID: 20876832.

Marson et al. "Connecting microRNA genes to the core transcriptional regulatory circuitry of embryonic stem cells" Cell 134, 3 (Aug. 2008), 521-533. PMID: 18692474.

Mencia et al. "Mutations in the seed region of human miR 96 are responsible for nonsyndromic progressive hearing loss" Nature Genetics 41, 5 (May 2009), 609-613. PMID: 19363479.

Morin et al. "Application of massively parallel sequencing to microRNA profiling and discovery in human embryonic stem cells" Genome Research 18, 4 (Apr. 2008), 610-621. PMID:18285502.

Nandakumar et al. "RNA ligase structures reveal the basis for RNA specificity and conformational changes that drive ligation forward" Cell 127, 1 (2006), 71-84.

Olson et al. "Analysis of large-scale sequencing of small RNA" Pacific Symposium on Biocomputing. Pacific Symposium on Biocomputing (2008), 126-136. PMID: 18229681.

Pfeffer et al. "Cloning of small RNA molecules" Current Protocols in Molecular Biology / Edited by Frederick M. Ausubel . . . et a l Chapter 26 (Nov. 2005), Unit 26.4. PMID: 18265364.

Romaniuk et al. "The effect of acceptor oligoribonucleotide sequence on the t4 RNA ligase reaction" European Journal of Biochemistry / FEBS 125, 3(Jul. 1982), 639-643. PMID: 7117259.

Shi et al. "Facile means for quantifying microRNA expression by real-time PCR" BioTechniques 39, 4 (Oct. 2005), 519-525. PMID:16235564.

Shi et al. "MicroRNA regulation of neural stem cells and neurogenesis" The Journal of Neuroscience: The Official Journal of the Society for Neuroscience 30, 45 (Nov. 2010), 14931-14936. PMID21068294.

Small et al. "Pervasive roles of microRNAs in cardiovascular biology" Nature 469, 7330 (Jan. 2011), 336-342. PMID: 21248840.

Tam et al. "Pseudogene-derived small interfering RNAs regulate gene expression in mouse oocytes" Nature 453, 7194 (May 2008), 534-538. PMID: 18404147.

Wang et al. "Oligoribonucleotide circularization by 'template-mediated' ligation with t4 RNA ligase: synthesis of circular hammerhead ribozymes" Nucleic Acids Research 26, 10 (May 1998), 2502-2504. PMID: 9580707.

Wang et al. "Mutational analysis of bacteriophage t4 RNA ligase 1" Journal of Biological Chemistry 278, 32 (2003), 29454-29462.

International Search Report/Written Opinion for PCT Application No. PCT/US2012/037746 issued Nov. 9, 2012.

International Preliminary Report on Patentability for PCT Application No. PCT/US2012/037746 issued Nov. 19, 2013.

Bawankar et al. ""5' and 3' End Modifications of Spliceosomal RNAs in Plasmodium Falciparum Molecular Biology Reports, vol. 37, pp. 2125-2133 (Aug. 2009).

* cited by examiner

POOLED ADAPTER STRATEGY FOR REDUCING BIAS IN SMALL RNA CHARACTERIZATION

PRIORITY CLAIM

This application claims the benefit of U.S. Provisional Application No. 61/486,214 filed on May 13, 2011.

BACKGROUND OF THE INVENTION

1. Field of the Invention

The disclosure relates generally to the field of nucleic acid sequence determination and, more specifically, to deep sequencing approaches to parallel sequence determinations of nucleic acids, e.g., small RNAs, microRNAs, piRNAs.

2. Description of the Relevant Art

Small RNA sequencing (sRNA-seq) is now the gold standard for small RNA profiling and discovery in fields such as the study of biomarkers in cancer, differentiation in stem cells and transposon silencing in the germline. Biases in deep sequencing which affect the profiling have been reported, but their etiology has not been identified.

The advent of deep sequencing has now made it possible to sequence the full complement of small RNAs in a cell. Small RNAs (15-30 nucleotides or nts) play an important role in a variety of cellular processes. MicroRNAs, piRNAs and endogenous siRNAs are among the many small RNAs that are crucial regulators of genetic activity. Small RNA profiling through deep sequencing has become important for understanding the biology of these genes and for identifying miRNA markers for diagnostic and therapeutic uses. Real-time PCR (RT-PCR) and microarrays can be used to profile known small RNAs but a better approach to identifying differences between closely related microRNAs, and to the discovery of novel sequences, is deep sequencing. Subtle variations, such as found in isomers, and modifications, such as uridylation, cannot be detected by microarrays or RT-PCR. In addition, microarrays and RT-PCR also suffer from cross-hybridization artifacts. Deep sequencing is especially attractive for its sensitivity to low abundance transcripts. In light of these benefits of deep sequencing, a persistent mystery in the field of small RNA sequencing is the discrepancy between the results from deep sequencing, microarrays and qPCR.

Accordingly, a need continues to exist in the art for unbiased methods of efficiently and accurately profiling the RNAs of a biological sample such as a cell. A need also continues to exist for deep sequencing techniques that show a reduced, or absent, bias in sequenced RNAs.

SUMMARY OF THE INVENTION

Accurate quantification of nucleic acids using deep sequencing is undermined by any bias introduced during the processing or manipulation of those nucleic acids during characterization and, in the case of small RNA characterization such as microRNA (miRNA) or piwi RNA (piRNA) characterization, the particular sRNA (e.g., miRNAs) could be under or over-represented. This would call into question quantitative data from deep sequencing, especially when used to assess the relative abundance of isoforms and variants. Although biases might also affect other profiling platforms, the potential presence of these biases in small RNA sequencing, or sRNA-seq, would undermine the incredible sensitivity and accuracy made possible by deep sequencing. For piRNAs, sequence features such as the Tbias at the 5' end are obtained by profiling the nucleotide bias at each position of the sequence. This information can provide clues to the biogenesis of these piRNAs. A data set that is biased by collection methods can, therefore, lead to erroneous conclusions. Accordingly, the disclosure identifies the problem of bias in nucleic acid manipulation, e.g., nucleic acid derivatization with adapters and nucleic acid amplification, such as would be found in characterizing sRNA.

The disclosed subject matter provides materials and methods for characterizing nucleic acids, including characterizing nucleic acid populations. For example, the disclosure provides materials and methods for preparing nucleic acids to be deep-sequenced, such as by preparing cellular RNAs for deep sequencing. The materials and methods of the disclosure exhibit reduced or non-existent bias in terms of RNAs amenable to manipulation, including the ligation of terminal adapters to RNAs and the amplification of such RNAs by any means known in the art. The sequencing of small RNAs, i.e., sRNA-seq, typically requires a series of isolation, ligation and amplification steps to prepare the sRNA of a cell or tissue into a library for sRNA-seq, or sequencing. Each of these steps involves some loss of material and, consequently, the sensitivity and accuracy of the sequencing decreases. Upon investigation of each of these steps, it has been discovered that a reproducible discrepancy can arise in the ligation or amplification steps.

The most widely used technique of sRNA-seq involves the addition of 3' and 5' adapters onto the ends of the small RNAs by direct RNA ligation using T4-RNA ligases (Rnl2 and Rnl1 respectively, FIG. 1), followed by an amplification step. Each of the steps in sample preparation results in some loss of material, but it has been assumed that these losses are non-specific. If there were any biases introduced in the ligation steps, however, it would result in errors that are not easy to correct, especially since RNA ligases are known to have biases that have not been explored in the context of their use in deep sequencing. Thus, disclosed herein is a systematic investigation of the presence and source of biases in sRNA-seq. Small RNAs from 293T human kidney-derived cells and mouse embryonic stem (mES) cells were deep sequenced, using strategies aimed at identifying the source(s) of bias(es). The data reveals that a reproducible discrepancy can arise in the ligation or amplification steps. Specifically, the T4-RNA ligases used in sample preparation are the predominant causes of distortions arising during RNA ligase-mediated sequence-specific ligations. These biases can be overcome using a pooled adapter strategy. The data provides a basis for new insight into the efficiency of RNA-ligases through deep sequencing, and provides an invaluable strategy to reduce biases in RNA libraries and thereby obtain a more accurate profile of the small RNA transcriptome.

To address the issue of bias, sequence biases in ligase activity were examined and characterized, revealing the consequences of these biases on the results of sequencing. Through a comprehensive series of small RNA sequencing experiments, using sequencing adapters with different termini and miRNA samples from different tissues, it has been established that the RNA-ligases have strong sequence-specific biases, which significantly distort the miRNA profiles. In response to these findings, a pooled adapter strategy has been devised that overcomes this bias. A comparison of the sequencing data to microarray and qPCR data further establishes the accuracy of this method. In light of the results disclosed herein, published small RNA profiles as well as barcoding strategies using adapter-end modifications, are expected to be misleading due to the effect of bias. By providing a wide spectrum of substrate for the ligase, the pooled-adapter strategy disclosed herein provides a means to overcome issues of bias, and to generate more accurate small RNA profiles.

Various aspects of the disclosed subject matter are described in the following paragraphs.

A set of pooled 5' RNA adapters for small RNA characterization is composed of a plurality of adapter bases that are covalently extended at the 3' ends by addition of a nucleotide (nt 1), wherein covalently bound nt1 is selected from the group consisting of guanylate, adenylate, uridylate, cytidylate, inosine monophosphate, and 5-bromouridylate, thereby yielding a set of pooled 5' RNA adapters. In some embodiments, the 3' nucleotide is selected from the group consisting of guanylate, adenylate, uridylate and cytidylate. Each adapter of unique sequence may be present in about equimolar concentration relative to other adapters in the pool.

In some embodiments, the pooled 5' RNA adapters also include a nucleotide 2 (nt2) covalently bound 3' to nt1, wherein the covalently bound nt2 is a nucleotide selected from the group consisting of guanylate, adenylate, uridylate, cytidylate, inosine monophosphate, and 5-bromouridylate. Additionally, a nucleotide 3 (nt3) may be covalently bound 3' to nt2 and a nucleotide 4 (nt4) covalently bound 3' to nt3, wherein each of covalently bound nt3 and nt4 is a nucleotide selected from the group consisting of guanylate, adenylate, uridylate, cytidylate, inosine monophosphate and 5-bromouridylate. In some embodiments, each adapter comprises a PCR primer binding site. In other embodiments, each adapter comprises a restriction endonuclease cleavage site.

In an embodiment, a set of pooled 3' adapters for small RNA characterization is composed of a plurality of adapter bases that are covalently extended at the 5' ends by addition of a nucleotide (nt 1), and wherein the covalently bound nt1 is selected from the group consisting of deoxyguanylate, deoxyadenylate, thymidylate, deoxycytidylate, guanylate, adenylate, uridylate, cytidylate, deoxyinosine monophosphate, inosine monophosphate, deoxy-5-bromouridylate and 5-bromouridylate. The pooled 3' adapters, in some embodiments, may be pooled 3' DNA adapters. Each adapter of unique sequence may be present in about equimolar concentration relative to other adapters in the pool.

The pooled 3' DNA may also include a nucleotide 2 (nt2) covalently bound 5' to nt1 and wherein covalently bound nt2 is a nucleotide selected from the group consisting of deoxyguanylate, deoxyadenylate, thymidylate, deoxycytidylate, deoxyinosine monophosphate, and deoxy-5-bromouridylate. In some embodiments, a nucleotide 3 (nt3) may be covalently bound 5' to nt2 and a nucleotide 4 (nt4) may be covalently bound 5' to nt3, wherein each of covalently bound nt3 and nt4 is a nucleotide selected from the group consisting of deoxyguanylate, deoxyadenylate, thymidylate, deoxycytidylate, deoxyinosine monophosphate and deoxy-5-bromouridylate. In some embodiments, each adapter comprises a PCR primer binding site. In other embodiments, each adapter comprises a restriction endonuclease cleavage site.

In an embodiment, a kit for amplifying small RNA includes a set of pooled 5' DNA adapters and a set of pooled 3' adapters, as described above. In one embodiment, the set of pooled 3' adapters is a set of pooled 3' DNA adapters. The kit may also include a T4 RNA Ligase 1 (Rnl1) and a T4 RNA Ligase 2 (Rnl2). The kit may also include a truncated T4 RNA ligase 2.

A method of profiling small RNA in a sample includes:
(a) contacting the sample with a set of pooled 5' DNA adapters and a set of pooled 3' adapters as described above;
(b) ligating the adapters to the small RNA in the sample;
(c) amplifying the ligated small RNAs; and
(d) detecting amplified small RNAs, thereby profiling the small RNAs.

In some embodiments, the small RNAs in the sample are contacted separately by the pooled 5' DNA adapters and pooled 3' DNA adapters. The small RNAs may be contacted by the pooled 3' DNA adapters in the absence of ATP.

The 5' RNA adapters may ligated to the small RNAs using Rnl1 RNA Ligase. The 3' adapters may be ligated to the small RNAs using Rnl2 RNA Ligase. Ligating the 3' adapter to small RNAs may be mediated by truncated T4 RNA Ligase 2.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
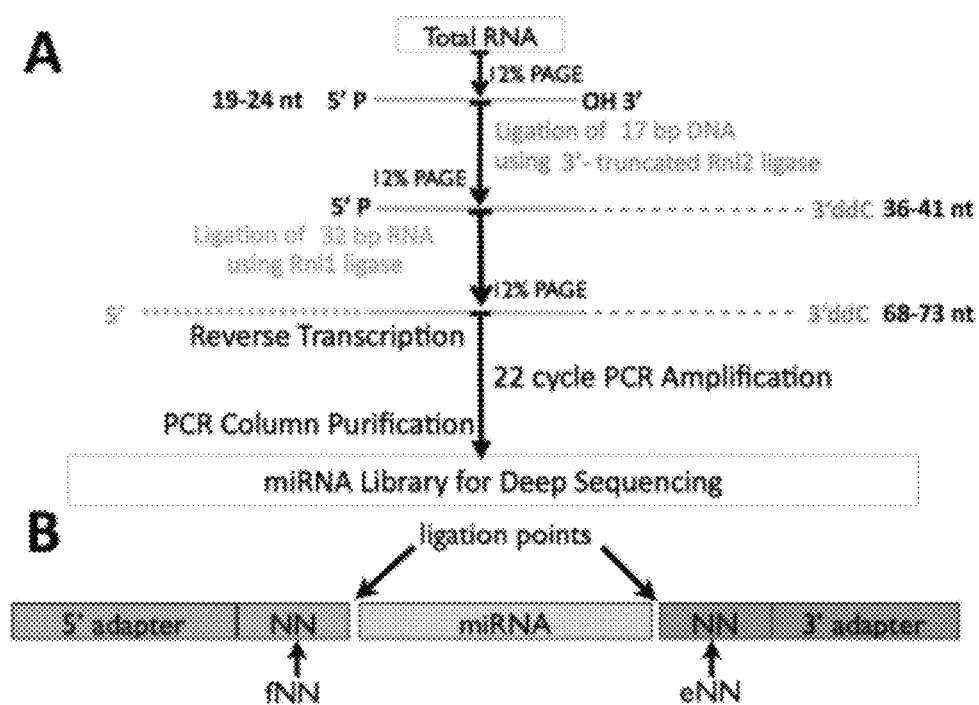
FIG. 1 depicts a protocol for preparing samples for small RNA sequencing.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

The disclosure provides an approach to the characterization of nucleic acid samples, e.g., cell, tissue or organ small RNAs, that addresses the issue of bias in adapter ligation to small RNAs by providing a pool of adapters modified at the termini ligated or to be ligated to the small RNAs. The adapter modifications involve the covalent addition of at least two or more mixed nucleotides to the ligated or to be ligated terminus of each 5' adapter base and each 3' adapter base. An adapter base may be any adapter known in the art provided that the compound has not yet been modified by terminal addition of mixed nucleotides. Thus, the disclosure provides a set of pooled 5' adapters containing at least two mixed nucleotides at the 3' termini available for ligation to the 5' end of small RNAs. Also provided is a set of 3' adapters containing at least two mixed nucleotides at the 5' termini available for ligation to the 3' end of small RNAs. By mixed nucleotide is meant more than one nucleotide available for incorporation into the set of adapters at a given position. For the 5' adapter, at least the two nucleotide positions at the 3' end of the adapter are added using mixed nucleotides, creating a set of 5' adapters containing individual adapters having in common the sequence of the adapter base, but having at the 3' end of the sequence any one of the mixed nucleotides at positions 1 and 2, where position 1 is at the 3' terminus and position 2 is adjacent thereto. The mixed nucleotides typically will contain each of the four conventional nucleotides appropriate to the type of DNA adapter base (DNA or RNA), but the mixed nucleotides may instead contain, or contain in addition, any nucleotide analog known in the art, such as inosine monophosphate, deoxyinosine monophosphate, 5-bromouridylate or deoxy-5-bromouridylate. For the 3' adapter, at least the two nucleotides at the 5' end of the adapter are added using a set of the above-described mixed nucleotides appropriate to the adapter being modified (DNA or RNA).

In some embodiments, a pool of adapter bases may include between 1 and 25 nucleotide bases. As used herein the term "randomized adapters" refers to adapter bases whose ends are extended by 1 to 25 nucleotide bases that vary by nucleotide composition in a random or arbitrary manner. The ends of the randomized adapters may be composed of equal or weighted DNA, RNA nucleotides.

In some embodiments, the adapter modification, i.e., the nucleotide addition to the adapter base, involves one, two, three, four or more nucleotides covalently bound to the 5' end of a 3' adapter or to the 3' end of a 5' adapter. Preferred are modifications comprising one, two, three, four or more covalently bound nucleotides. Preferred nucleotide modifications are collectively fully mixed in that, for each added position in the adapter, each of the four conventional nucleotides (e.g., ribo- or deoxyribo-G, A, U/T and C, as appropriate depending on the nature of the adapter base (DNA or RNA)) are used in approximately equal amounts for synthesis using any technique known in the art. Also contemplated are additions to the 3' terminus of a 5' adapter and the 5' terminus of a 3' adapter that have equal or differing numbers of added mixed nucleotides. Beyond the use of nucleotide that are fully mixed at each position, the disclosure contemplates individual positions that are, collectively, partially mixed nucleotides or that are single nucleotides. In particular, as experience with particular adapters and adapter bases is developed, it is expected that an understanding will develop regarding the bias of particular RNA Ligases with respect to particular adapter base sequences such that the preferred terminal nucleotide(s) are known and can be engineered to be present in each adapter used in a ligation attaching the adapter to a small RNA.

The disclosure also comprehends the use of unconventional nucleotides in nucleotide-based modifications by covalent addition to adapter bases. For example, one or more added positions is occupied by (ribo- or deoxyribo-) IMP, 5-bromouridylate, and/or other unconventional nucleotides or nucleotide analogs known in the art. Apparent from the description herein, the additions to the adapter bases will be useful in modifying any of a wide variety of adapter bases and the modifications by covalent additions are not limited to particular adapter bases or adapter bases of particular nucleic acid sequence(s). It will be appreciated that the adapter bases disclosed herein, see, e.g., Table 1, are adapters of any useful or desired sequence, including adapters known in the art.

To aid in understanding the detailed description of the compositions and methods according to the disclosure, a few express definitions are provided to facilitate an unambiguous disclosure of the various aspects of the disclosure.

An "adapter base" is a nucleic acid adapter with termini that have not been modified in accordance with the present disclosure. An "adapter" or "modified adapter" refers to an adapter base modified by addition of at least one nucleotide to at least one terminus of the adapter base. Typically, adapters or modified adapters will be covalently linked to sRNA, or the corresponding DNA molecule, or the DNA complement of the sRNA for use in manipulating the construct or characterizing the construct or sRNA sequence, or its DNA counterpart or complement.

A nucleic acid "modification" is a chemical alteration to a nucleic acid molecule. Preferably, a nucleic acid modification is the covalent addition to one of the two termini of an adapter base. For 5' adapters, i.e., adapters ligated or to be ligated to the 5' end of a small RNA, the modification(s) occur at the 3' terminus of the adapter base to yield the adapter. For 3' adapters, i.e., adapters ligated or to be ligated to the 3' end of a small RNA, the modification(s) occur at the 5' terminus of the adapter base to yield the adapter. A sRNA joined to adapters will have two bound adapters, and these adapters may be the same or different. The adapters typically provide functionality useful in sRNA manipulations to characterize the sRNA, such as including a PCR primer binding site, a restriction site(s) useful for sizing and/or cloning the sRNA or a product (e.g., cDNA) made therefrom.

An "sRNA" is a small RNA as that term is understood in the art and includes microRNA (miRNA) and piwiRNA (piRNA). Apparent from their use in context herein, these terms may be used interchangeably. Typically, sRNA molecules are involved in at least one aspect of regulating cell physiology, such as involvement in the regulation of the expression of one or more genes.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1 discloses the materials and methods used in the experiments described herein. Example 2 describes many of the experiments reported herein, including the construction of sRNA libraries using various modified adapter bases which may be 5' or 3' adapters. Example 3 addresses the biases revealed in the experiments and models for reducing or eliminating bias.

Example 1

This Example provides a disclosure of the materials and methods used in conducting the experiments disclosed in the remaining working examples.
ES Cell Culture R1 mouse ES cell line was cultured feeder-free on 0.1% gelatin-coated plates in DMEM; Hi-Glucose, 15% fetal bovine serum, non-essential amino acids, L-glutamine, β-mercaptoethanol, penicillin/streptomycin, sodium pyruvate and leukemia inhibitory factor (LIF). Cells were grown in a humidified incubator in 5% C02 and 95% air. These cells were kindly donated by the Lemischka laboratory at Mount Sinai School of Medicine.
Library Construction and Sequencing Total RNA was isolated from 293T cells and mouse embryonic fibroblasts using Trizol extraction (Invitrogen). Sequencing libraries enriched for micro RNAs were constructed using a modified version of a small RNA protocol detailed by Pfeffer (Pfeffer et al. "Cloning of small RNA molecules." *Current Protocols in Molecular Biology*/Edited by Frederick M. Ausubel . . . et al, Chapter 26 (November 2005), Unit 26.4. PMID: 18265364). Two RNA markers were synthesized Spike 19 (CGUACGGUUUAAAC-UUCGA; SEQ ID NO:1) and Spike 24 (CGUACG-GUUUAAACUUCGAAAUGU; SEQ ID NO:2) (Sigma Aldrich). RNA was end-labeled using polynucleotide kinase and radioactive ATP (P32). Ten micrograms of total RNA was size fractionated by denaturing polyacrylamide gel electrophoresis (PAGE, 12% gel). miRNAs were excised from the gel using radiolabeled markers as guides. Purified miRNA was ligated to a 17 nt 3' adapter with truncated T4 RNA ligase 2 (Rnl2) in an ATP-free buffer (BioScientific). The ligated fragment of 36-41 nt was PAGE purified. A second RNA adapter was ligated to the 5' side of the product using T4 RNA ligase 1 (Rnl1) and buffer containing ATP. The 72-78 nucleotide ligated fragment was PAGE purified and then reverse transcribed using a specific primer (BanI-RT; ATTGATGGTGCCTACAG; SEQ ID NO:3). cDNA was amplified by 22 cycles of PCR with primers that incorporate sequences compatible with the Illumina platform (Sol-5-SBS, AATGATACGGCGACCACCGAACACTCTTTC-CCTACACGACG, SEQ ID NO:4 and Sol-3-ModBan, CAAGCAGAAGACGGCATACGATTGATGGTGCCTA-CAG; SEQ ID NO:5) (FIG. 1). The library was sequenced using the Illumina Genome Analyzer IIx at 36-nucleotide read length.
Microarray miRNA abundance was assessed in 293T and mES RNA samples by oligonucleotide microarray using Affymetrix GeneChip (miRNA 1.0). One µg of total RNA was labeled using the FlashTag Biotin 3DNA kit (Genisphere), as follows: polyadenylation of RNA by polymerase, ligation to a biotinylated 3DNA molecule mediated by an oligonucleotide with 5' polyd(T) and 3' 3DNA complementary adapter. Labeled RNA was hybridized to the microarray using standard Affymetrix methods. Fluorescence intensities were extracted using the R statistical package, using methods from the BioConductor module.
Real-Time PCR Quantitative real-time PCR was carried out using the Applied Biosystems (AB) microRNA specific reagents and a 7900HT thermocycler. Ten ng of total RNA were reverse transcribed with a miRNA-specific hairpin primer using the AB micoRNA Reverse Transcription kit. Specific forward primers and universal reverse primers were random with cDNA and AB Universal PCR Master Mix (no UNG) as recommended by the manufacturer. The following miRNAs were assayed: hsa-mir-18a, -20a, -106b, -92a, -103-2, -10, -16, -17 and hsa-let-7. Ct values were extracted from real-time data using the auto threshold setting.
Computational Analysis Analysis of such datasets is well established, but extracting the inserts from the libraries was complicated by three causes: (1) sequencing errors that miscall a base, (2) sequencing errors that miss a base, and (3) errors in the synthesis of the NN constructs. To mitigate problems from sequencing errors, we only accepted sequences where the 3' adapter sequences were matched exactly. This eliminates most of the problematic reads, but does not solve the issue of point 3 above. For that, we used the relative abundances of the various inserts in the small RNA library (from our analysis of data from several runs), to identify synthesis errors. Failure to synthesize a particular N, or a skew in a particular N, could give rise to a misidentification of the origin of the sequence (which library it came from), or its end-modifications. Each sequence was binned into the appropriate NN category, as well as the appropriate version of the miRNA sequence (the canonical mature or some variant, either derived from the original hairpin sequence or a non-template modification). Most of the processing was done using custom Perl scripts. Custom R-scripts were used to generate the graphs and statistical analyses.

Example 2

In order to establish if the ligation of adapters to small RNAs was sequence dependent, libraries were constructed for small RNA sequencing, by customizing the standard protocol (FIG. 1), using modified adapters. Total RNA is size fractionated by denaturing polyacrylamide gel electrophoresis (PAGE) and miRNAs are excised from the gel using radiolabeled markers as guides. Purified small RNAs are ligated, using a truncated T4 RNA ligase 2 (Rnl2) in an ATP-free buffer, to a 17 nt modified 3' DNA adapter with a dideoxy nt at the 3' end and an activated adenylation at the 5' end. The dideoxy nt (more specifically, the deoxy 3' carbon of the 3'-terminal nt) prevents selfligation of the adapter, while the truncated ligase prevents circularization of the small RNA inserts. The ligated fragment of 36-41 nt is then PAGE-purified to remove the unligated 3' adapters. A 32 nt RNA adapter is ligated to the 5' side of the product using T4 RNA ligase 1 (Rnl1). The 72-78 nt ligated fragment is PAGE-purified again to remove the unligated 5' adapters. The product is reverse-transcribed using a specific primer and the resulting cDNA is amplified by PCR with primers that incorporate sequences compatible with a deep-sequencing platform.

Strategies Using Modified Adapters

To understand the exact nature of biases, we devised strategies using various 5' and 3' adapters with additions to the ligating ends (3'-end of the 5' adapter and the 5'-end of the 3' adapter). We devised six strategies involving these adapter pools, as listed below and in Table 1.

Figure 2:
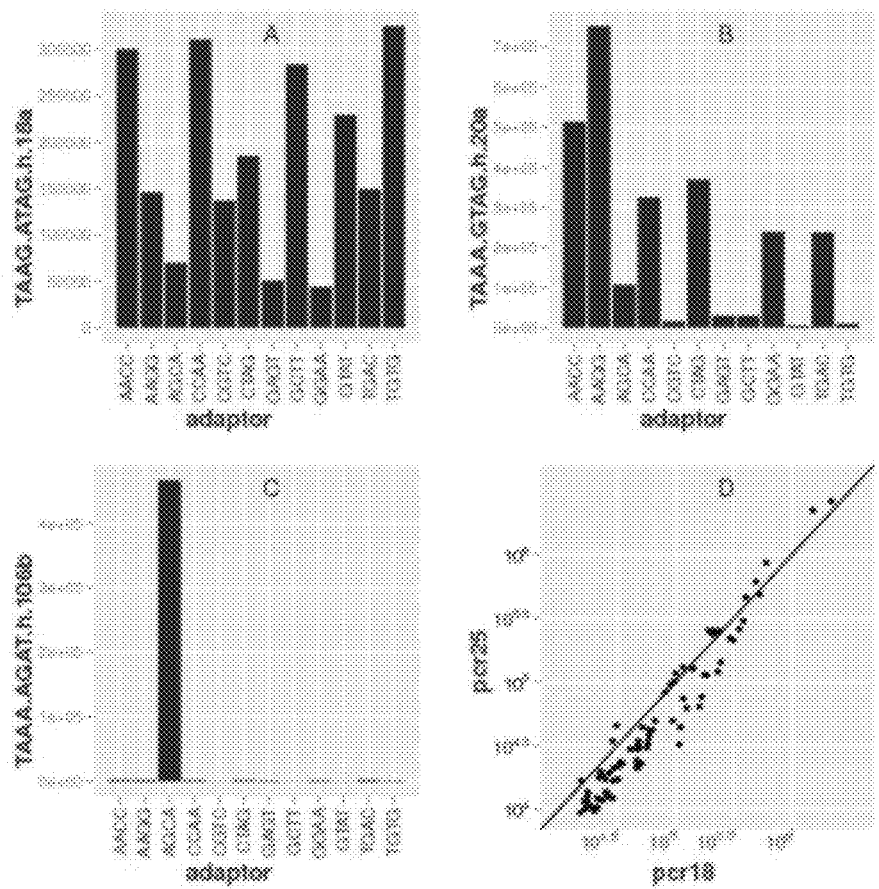
FIG. 2A depicts a histogram of mi RNA abundance for miR-18a microRNAs.
FIG. 2B depicts a histogram of mi RNA abundance for miR-20a microRNAs.
FIG. 2C depicts a histogram of mi RNA abundance for miR-106b microRNAs.
FIG. 2D depicts an analysis of the effect of PCR cycles on the results.

1. noNN, uses the standard modban 5' and 3' adapters.
2. 4-mer pool, the standard modban 3' adapter, pool of twelve 5' adapters with 4-mer additions.
3. fNN, uses the standard 3' adapter and a pool of 5' adapters generated by adding random NN additions to the 3' end of the 5' modban adapter.
4. eNN, uses the standard 5' adapter with a pool of 3' adapters that are modified at the 5' end with NN additions (eNN).
5. fNN eNN, uses a pool of 5' and 3' adapters with the NN modifications described in 3 and 4.
6. fNNNN, uses a pool of 5' modban adapters with the addition of random NNNN to the 3' end and the standard 3' adapter.

from 293T cells, using a pool of twelve 5' adapters, modified by the addition of 4-mers (TGAC, GAGT, GTAT, CGTC, GGAA, AAGG, GCTT, AACC, CCAA, AGCA, CTAG, and TGTG). The results showed significant bias with little similarity between data from different adapters (FIG. 2). Sequencing libraries were constructed from total RNA derived from 293-T cells, using a pooled set of twelve 5' adapters that had different 4 mer 3' ends, shown on the x-axis. There is great diversity in the capture of individual miRNAs by different 5' adapters (FIGS. 2A, 2B and 2C show data for miR-18a, miR-20a and miR-106b microRNAs, respectively). FIG. 2C shows an extreme case where miR-106b is captured well by only one adapter, ending in AGCA, out of the 12 adapters constituting the pool. These data are consistently reproduced in other experiments shown in FIG. 4. To isolate the effect of PCR cycles, samples were prepared twice, using 25 (y-axis) and 18 (x-axis) cycles of PCR (FIG. 2D). Each point represents a miRNA. The correlation between the two sets of PCR conditions is high (coefficient of 0.95) and the best linear fit to the points is a line of slope 1, indicating that the data are reproducible and PCR is not responsible for the biases.

We also prepared individual 293T cell samples using one adapter per sample, selecting five 4-mer ends (TGAC,

TABLE 1

| Strategy | 5' adapter RNA | 3' adapter DNA |
|---|---|---|
| noNN | ACACUCUUUCCCUACACGACGCUCUUCCGAUC<br>SEQ ID NO: 6 | CTGTAGGCACCATCAAT<br>SEQ ID NO: 7 |
| fNN | ACACUCUUUCCCUACACGACGCUCUUCCGAUCNN<br>SEQ ID NO: 8 | CTGTAGGCACCATCAAT<br>SEQ ID NO: 9 |
| fNNNN | ACACUCUUUCCCUACACGACGCUCUUCCGAUCNNNN<br>SEQ ID NO: 10 | CTGTAGGCACCATCAAT<br>SEQ ID NO: 11 |
| eNN | ACACUCUUUCCCUACACGACGCUCUUCCGAUC<br>SEQ ID NO: 12 | NNCTGTAGGCACCATCAAT<br>SEQ ID NO: 13 |
| fNN_eNN | ACACUCUUUCCCUACACGACGCUCUUCCGAUCNN<br>SEQ ID NO: 14 | NNCTGTAdGCACCATCAAT<br>SEQ ID NO: 15 |
| 4-mer pool | ACACUCUUUCCCUACACGACGCUCUUCCGAUCWXYZ<br>SEQ ID NO: 16 | CTGTAGGCACCATCAAT<br>SEQ ID NO: 17 |

Table 1 shows miRNA sequencing libraries that were generated with the adapter combinations shown. The 4-mer pool is a mixture of twelve adapters, represented as WXYZ (CTAG, GAGT, CCAA, AGCA, AACC, AAGG, TGAC, CGTC, GCTT, GTAT, GGAA, TGTG). All 3' DNA adapters have a 5' rAPP and 3'ddC modifications to prevent self-ligation and circularization.

5' Adapter Ligation Efficiency is Sequence Dependent

In order to determine if there was sequence dependent ligation of the 5' adapters, we prepared small RNA samples CGTC, AACC, GTAT and GGAA). We found wide variations in the miRNA profiles, especially for highly expressed miRNAs such as hsa-mir-20a and hsa-mir-18. In table 2, we see that replicates sequenced using different adapters have poor correlation to each other. When the adapters are pooled (Table 3), then there is concordance between the profiles for the different replicates. This indicates that a pooled approach would reduce the effect of biases due to adapter ligation on the 5' end.

TABLE 2

|  | B30_TGAC | B25_CGTC | 293T_AACC | B31_GTAT | B29_GGAA |
|---|---|---|---|---|---|
| B30_TGAC | 1 | 0.664 | 0.687 | 0.679 | 0.679 |
| B25_CGTC | 0.664 | 1 | 0.654 | 0.637 | 0.644 |
| 293T_AACC | 0.687 | 0.654 | 1 | 0.6 | 0.666 |
| B31_GTAT | 0.679 | 0.637 | 0.6 | 1 | 0.62 |
| B29_GGAA | 0.679 | 0.644 | 0.666 | 0.62 | 1 |

Table 2 depicts correlations between samples prepared using individual 5' adapters that differ only at the 3' terminus. The spearman-rank correlation is based on the rankings of the miRNA sequences by abundance. The relatively low correlations, between biological replicates of 293T cells, in contrast to the numbers seen in Table 3, suggests that the efficiency of ligation of the adapters to different miRNA sequences is quite variable. The row and column names reflect the samples and the adapter termini used, so B25 TGAC refers to sample B25 which uses the adapter ending in TGAC.

TABLE 3

| Samples | B26 | B30 | B25 | B29 |
|---|---|---|---|---|
| B26 | 1 | 0.91 | 0.96 | 0.95 |
| B30 | 0.91 | 1 | 0.91 | 0.92 |
| B25 | 0.96 | 0.91 | 1 | 0.97 |
| B29 | 0.95 | 0.92 | 0.97 | 1 |

Table 3 shows correlations between biological replicates of 293T cell samples, prepared using a pooled-adapter strategy. The correlations (spearman-rank) are based on the ranking of the miRNA sequences based on abundances calculated by averaging them over the five adapters listed in Table 1. This indicates that mixed pools of adapters will help overcome the biases in ligation efficiency.

Nature of Sequence Dependence in the Efficiency of 5' Adapter Ligation

Figure 3:
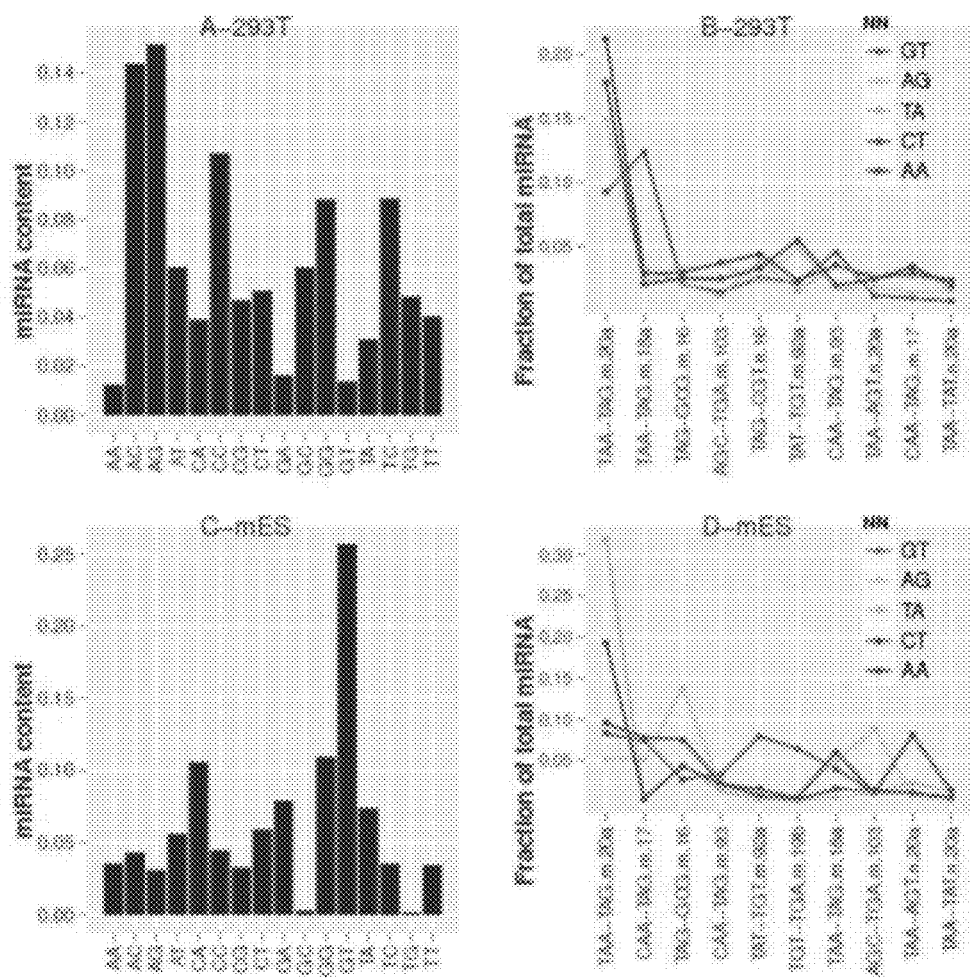
FIGS. 3A and 3C depict the fraction of miRNA measured by each adapter type, in 293T and mES samples, respectively.
FIGS. 3B and 3D depict the differences that arise from variations in the efficiencies that depend on the miRNA-adapter combination in 293T and mES, respectively.
Figure 4:
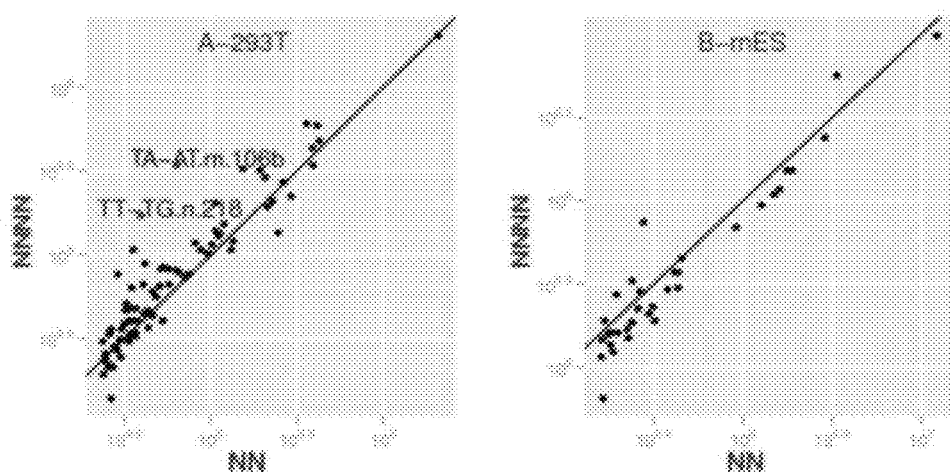
FIGS. 4A and 4B depict the effect of the two terminal 3' nts of the 5' adapter on T4-RNA ligase 1 (Rnl1) ligation efficiency.

To identify the biases inherent in the 5' adapter ligation, two samples from 293T and mES cells were prepared using the fNN strategy. The results showed that the profiles measured from the same sample can vary wildly for different adapters (FIG. 3). FIG. 3A (293T) and FIG. 3C (mES) depict the amount of miRNAs (y-axis) captured by each adapter (x-axis), suggesting some adapters are more efficient than others. If it were a simple matter of differing efficiencies for different adapters, then the miRNA profiles derived from each barcode should be scaled versions of each other. In fact, as shown in FIG. 2B (293T) and FIG. 2D (mES), the profiles for different adapters are very dissimilar. In FIG. 2B and FIG. 2D, the x-axis shows different miRNAs, ranked by their overall occurrence, which is the sum over all adapters. The y-axis shows, of the miRNAs captured by a particular adapter, the fraction that each miRNA occupies. It is apparent there can be dramatic shifts in the rankings for the miRNAs (the profiles) between adapters. We wanted to establish how much of the sequence proximal to the ligating end of the adapter determined the ligation efficiency. For this, we carried out an experiment using 5' adapters with 4 terminal random nucleotides, the fNNNN strategy. FIG. 4 shows that most of the ligation efficiency can be explained by the last two nucleotides. Only in one case, hsa-miR-106b, were the four nucleotides needed to pick out an abundant miRNA (see also FIG. 2 and FIG. 10).

Biases in 3' Adapter Ligation

We decided to investigate the bias on the 3' side, especially since the 3' adapter ligation is very different from the 5' adapter ligation. As explained in Example 1, it involves a truncated RNA-ligase (rn12) that needs an adenylated 3' adapter to carry out the ligation and the adapter is DNA.

We designed a simple gel-shift-based assay to test for the existence of a 3' adapter ligation bias. We chose two radio-actively labeled oligomers, a 19-mer (CGUACG-GUUUAAACUUCGA-SEQ ID NO: 18) and, a 24-mer that had a 5-mer (AAUGU) addition at the 3' end of the 19 mer. The RNA markers were 5' end-labeled with $^{32}$P and then ligated in duplicate to one of two sets of adenylated 3' DNA adapters. One set of 3' DNA adapters consisted of the standard (terminally unmodified) adapter with a 5' CTGT and the second set consisted of a mixture of adapters that differ from the standard adapter in having two extra mixed base (i.e., mixed nt) positions on the 5' side, with the start now becoming 5' NNCTGT. After ligation, the RNA-DNA products were size-fractionated on a 12% polyacrylamide gel.

Figure 5:
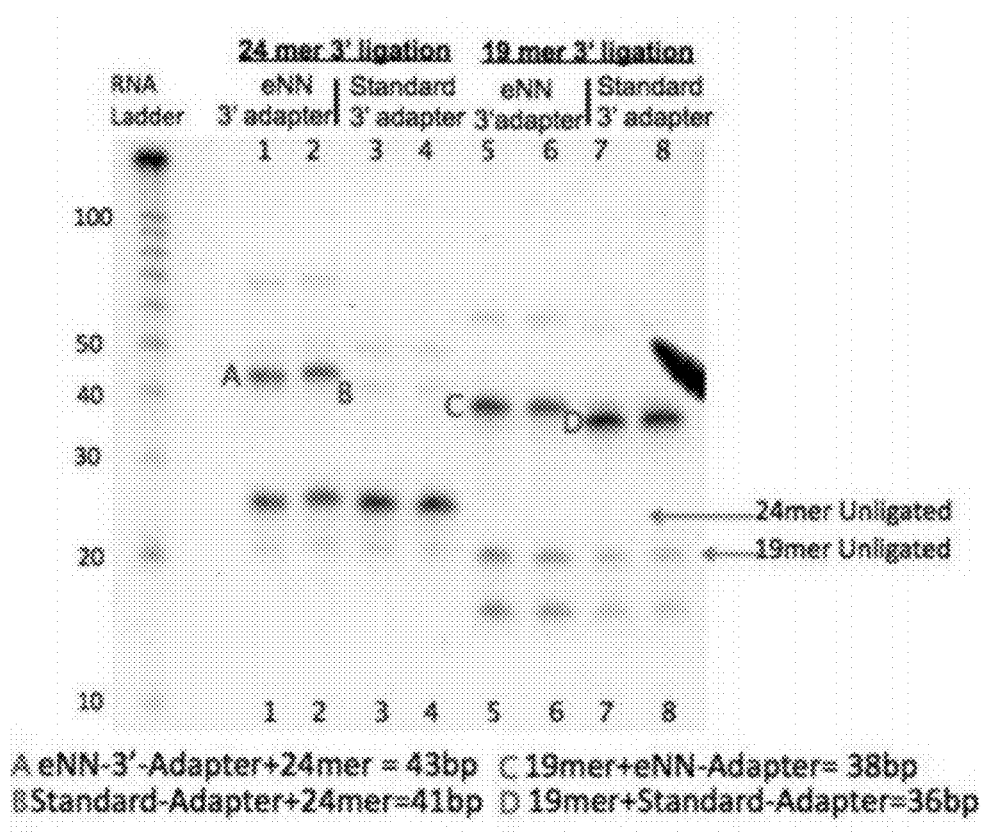
FIG. 5 shows that synthetic RNA ligation to a 3' adapter is enhanced by using a pool of 3' adapters with random NN at the 5' end.

FIG. 5 shows that with the standard 3' adapter, the 24-mer does not show good ligation, while the 19 mer shows good ligation, on the other hand, we have good ligation to both oligos with the eNN strategy. Specifically, the 19 nt marker ligated efficiently, irrespective of the adapters used (lanes 5-8), while the ligated 24-mer product is low in abundance when the standard adapter is used (lanes 1-2), but is efficiently ligated (with abundant products) when the mixed-bases adapters are used (lanes 3-4). This suggests two things, the 24 mer has good ligation only to certain members in the eNN pool, and that using a pool of adapters is better. While this may appear to be crude, the dramatic effect seen in the gel-shift suggests large differences in ligation efficiencies between different pairs of sequences, indicating that both the 5' and 3' adapter biases need to be taken into account in any sequencing experiment using T4-RNA ligases in the sample preparation.

Figure 6:
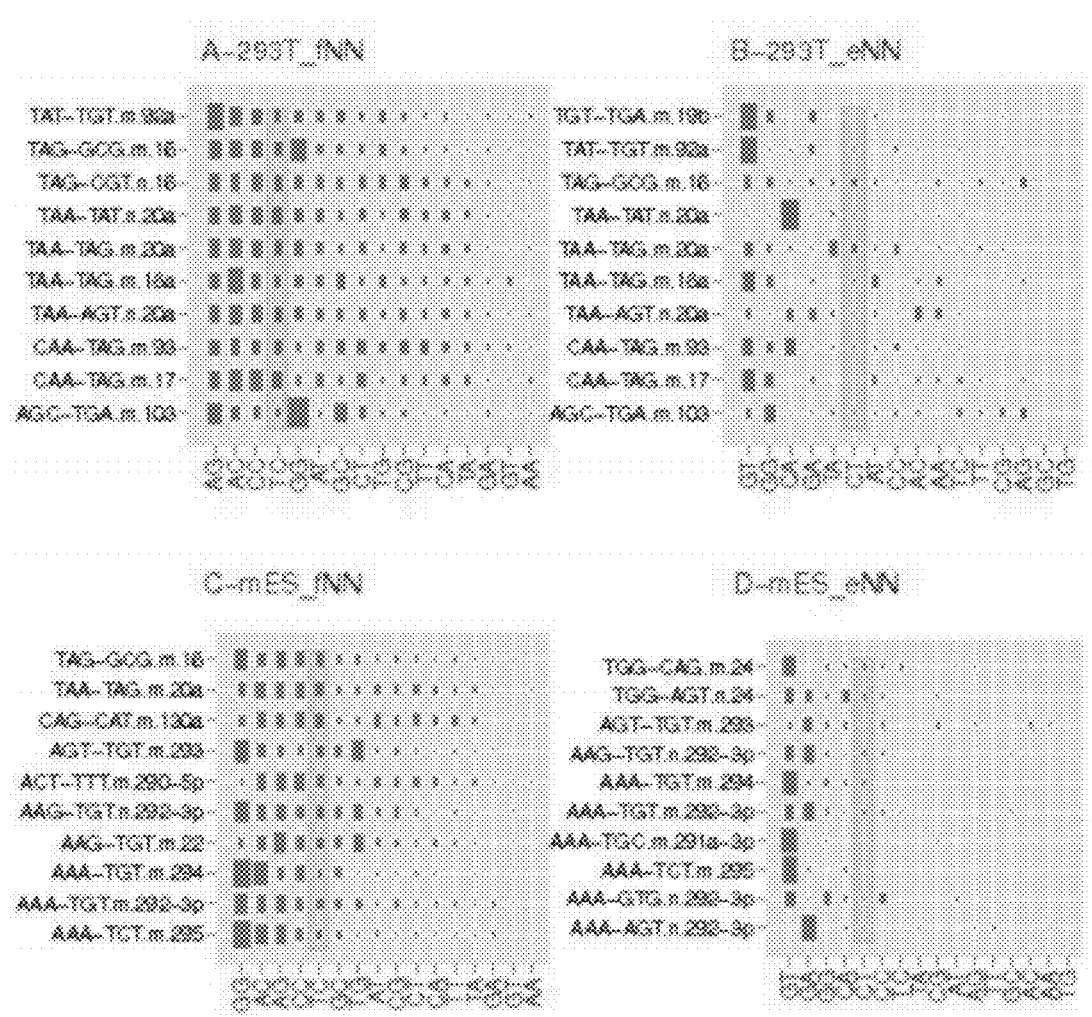
FIG. 6 depicts fluctuation plots showing ligation efficiencies for different fNN (A, C panels) and eNN (B, D panels) adapters against the most abundant miRNAs from 293T (A, B panels) and mES (C, D panels) cells.

We pursued a strategy similar to the case of 5' adapter ligation, using the eNN strategy for 3' adapters in order to systematically study the biases in the ligation of the 3' adapter. In FIG. 6, we show the efficiencies of the 5' and 3' adapter ligations in the form of a fluctuation graph. Fluctuation plots showing ligation efficiencies for different fNN (FIG. 6A, 6C) and eNN (FIG. 6B, 6D) adapters against the most abundant miRNAs from 293T (FIG. 6A, 6B) and mES (FIG. 6C, 6D) cells. "fNN" is defined in the description of FIG. 3. "eNN" refers to the addition of a mixed nt (A, G, U, C) to the two nucleotide positions at the 5' end of a 3' adapter, i.e., the end of the 3' adapter ligated to an sRNA. The naming convention of miRNAs in all the figures defines the beginning and end of the sequence followed by an "m" (for a canonical mature) or "n" for a non-canonical miRNA sequence followed by the name of the miRNA. The area of the dark rectangles depicts the value for each combination of miRNA and adapter. The standard adapter ends (TC at the 3' end in fNN and CT at the 5' end in eNN, highlighted in gray boxes) are not efficiently ligated to the most abundant miRNAs. Even the most efficient adapters show variability, indicating that no single adapter can be expected to work well across all possible sequences. For the most abundant miRNAs, most of the variability comes from the 3' adapter ligation (the eNN adapters, panels B, D). In mES cells, there are two isomers of mmu-miR-292-3p, the GT-ending 3' adapter captures the GAGT-ending isomer more efficiently, while the GA-ending 3' adapter captures the GAGTG-ending isomer more efficiently.

The 3' adapters show more variability, which is probably due to the greater diversity in the 3' ends of the miRNAs compared to the 5' ends, suggesting that the 3' adapter ligation might be a bigger source of biases in measurements. It is interesting to note that the efficiency of the standard modban adapters (the 5' one ends in TC and the 3' one starts with CT) is low, compared to some of the others, but there is no single adapter that is uniformly efficient across the miRNAs that we tested here. This again suggests that it is necessary to take a pooled approach on both adapters for an unbiased measurement.

A Model for Ligation Efficiencies

In order to develop a unified picture of the ligation efficiency and show that the experiments are consistent with each other, we developed a model. We propose a model for ligation efficiency based on the 256 combinations at each ligation junction, determined by the two nucleotides (16 possible combinations, AA, AC . . . TG, TT) on the ligating end of the adapter and the two nucleotides (16 possible combinations) on the ligating ends of the miRNA. We define these as Fij (i and j each varying from 1 through 16 where 1 stands for AA, 2 for AC going on to 15 for TG and 16 for TT) for the 5' adapter ligation, and Emn (m and n each varying from 1 through 16) for the 3' adapter ligation. Let Mk be the actual abundance of a miRNA labeled k in the sample. Let mk be the measured amount of miRNA labeled k using adapters with ends i and n on the 5' and 3' adapter respectively. Then, the following equation must hold true: $m^k = F_{ij} * M^k * E_{mn}$.

Figure 7:
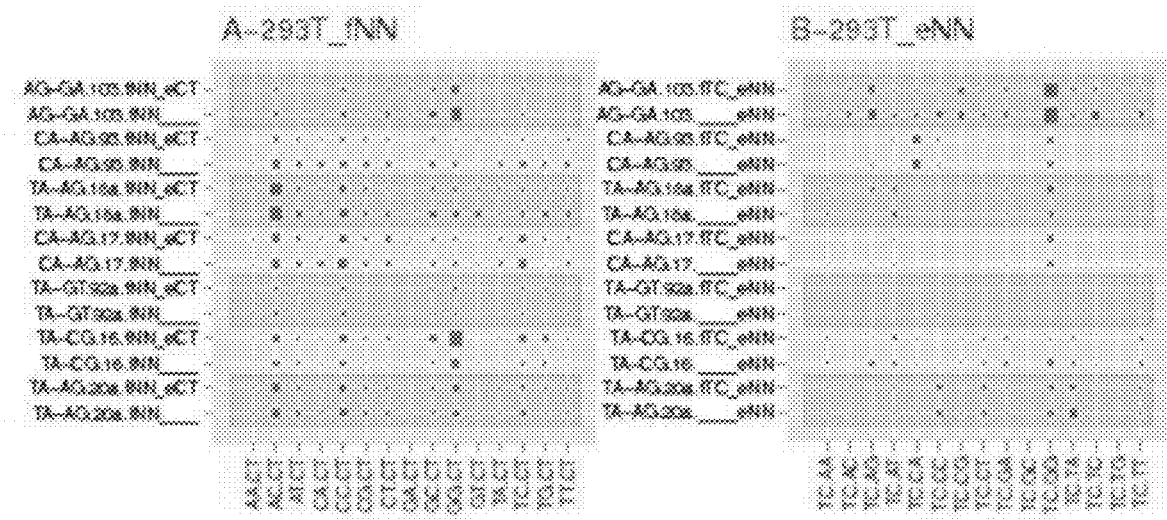
FIG. 7 depicts a comparison of parameters inferred from fNN (left panel) and eNN (right panel) against fNN eNN data.

The various adapter combinations are in equimolar concentrations; so they do not enter the equation (other than a constant that can be absorbed in F and/or E). FIG. 7 depicts a comparison of parameters inferred from fNN (left panel) and eNN (right panel) against fNN eNN data. The rows are miRNAs captured by different methods, alternate rows are data from the fNN eNN. In the figure fTC eNN means the f end was the standard (TC) and the e end varied, while fNN eCT means e end had a CT and the f end varied. In the data for fNN eCT versus fNN, the ratio to the AG-CT combination is depicted for each row. For the comparison of fNN eNN against eNN, the ratio of the values for the TC-GT combination was considered. The pairs are highlighted (either light- or dark-shaded rectangles), and the numbers between members of a pair are expected to be similar. There is a striking similarity between pairs of rows, indicating that the fNN eNN parameters are in concordance with separate measurements of parameters with fNN and eNN. An explanation for the model on which the calculations were based is provided herein below.

If this model is universal, we expect that the ratio between various F's (and various E's) from the fNN and eNN datasets should agree with the numbers derived from fNN-eNN. Since we do not know the Mk for a miRNA labeled k, we have to eliminate that from any quantity we measure. To do this, we pick the same value for eNN (CT) in the fNN eNN set as the 5' end on the 3' adapter in the fNN set. Within each experiment, we then define:

$$r_{ia}^k = m_{ii}^k / m_{aj}^k = F_{ij} / F_{aj} \quad (2)$$

$r_{ia}^k$, which is the ratio between the number of miRNA k, captured by adapters with ends i and a, is now independent of Mk and it should be identical for the fNN eNN (with eNN set at CT) and the fNN sets. We can do a similar comparison between the fNN eNN and the eNN sets. These ratios, derived from independent experiments, are shown in the fluctuation plot in FIG. 7. The numbers agree across miRNAs and across sample types, suggesting a level of universality for this model. The success of the model points to the reproducibility of the effects we have observed. Note, however, that miR-106b shows a bias that depends on the 4 nt at the 3' end of the 5' adapter (panel FIG. 2D and FIG. 4D).

Strategy to Overcome the Ligation Biases

Figure 8:
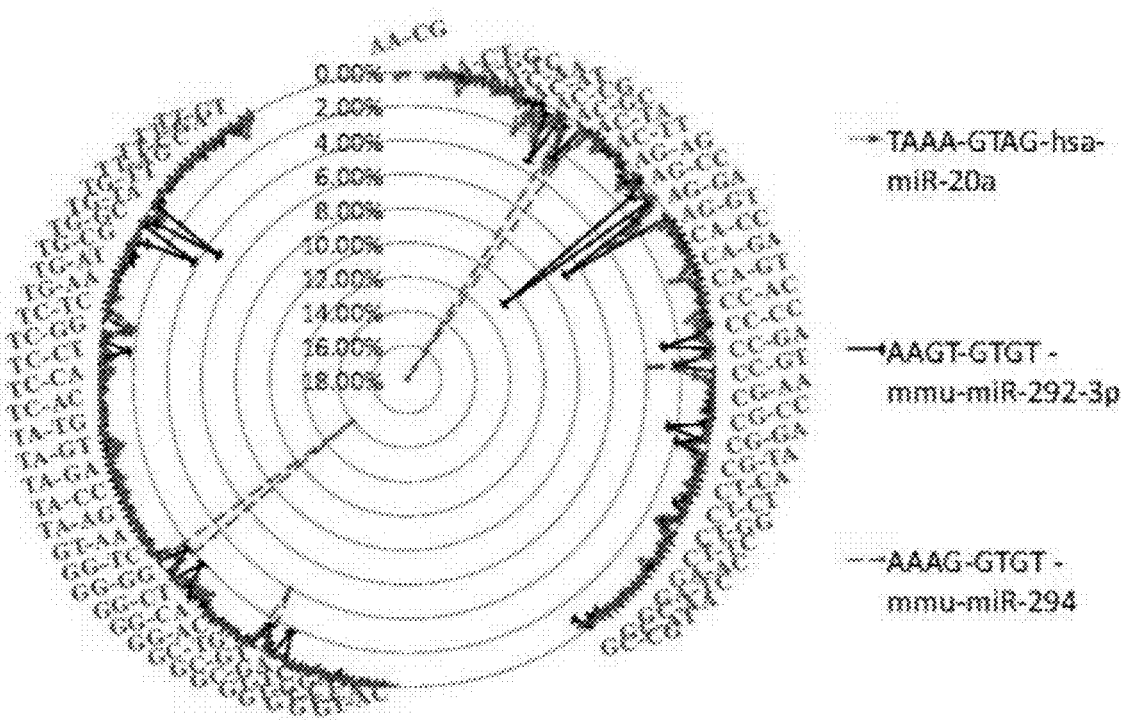
FIG. 8 depicts a radar plot showing the performance of different adapter termini combinations (fNN eNN)

Based on all the evidence presented above, we devised the fNN eNN strategy, described at the beginning of this section, to overcome the biases. We generated libraries for sequencing small RNA from the 293T and mES cells. FIG. 8 depicts a radar plot showing the performance of different adapter termini combinations (fNN eNN), shown outside the circle in blue. The inner circles represent percent contribution of each adapter combination to a particular miRNA that was sequenced. Data are presented for the top miRNA (hsa-miR-20a) in 293T cells and for the two top miRNAs (mmu-miR-292-3p and mmu-miR-294) from mouse embryonic stem cells. There was significant variation in the efficiency of capture between various combinations of 5' and 3' adapter end modifications. The data are consistent with adapter pooling, e.g., using the fNN eNN strategy, reducing the amount of starting material needed for sequencing small RNAs. Each microRNA seems to have a favored fNN-eNN pair that works best, once again suggesting the need for a pooled adapter approach.

Validity of the fNN eNN Strategy

Figure 9:
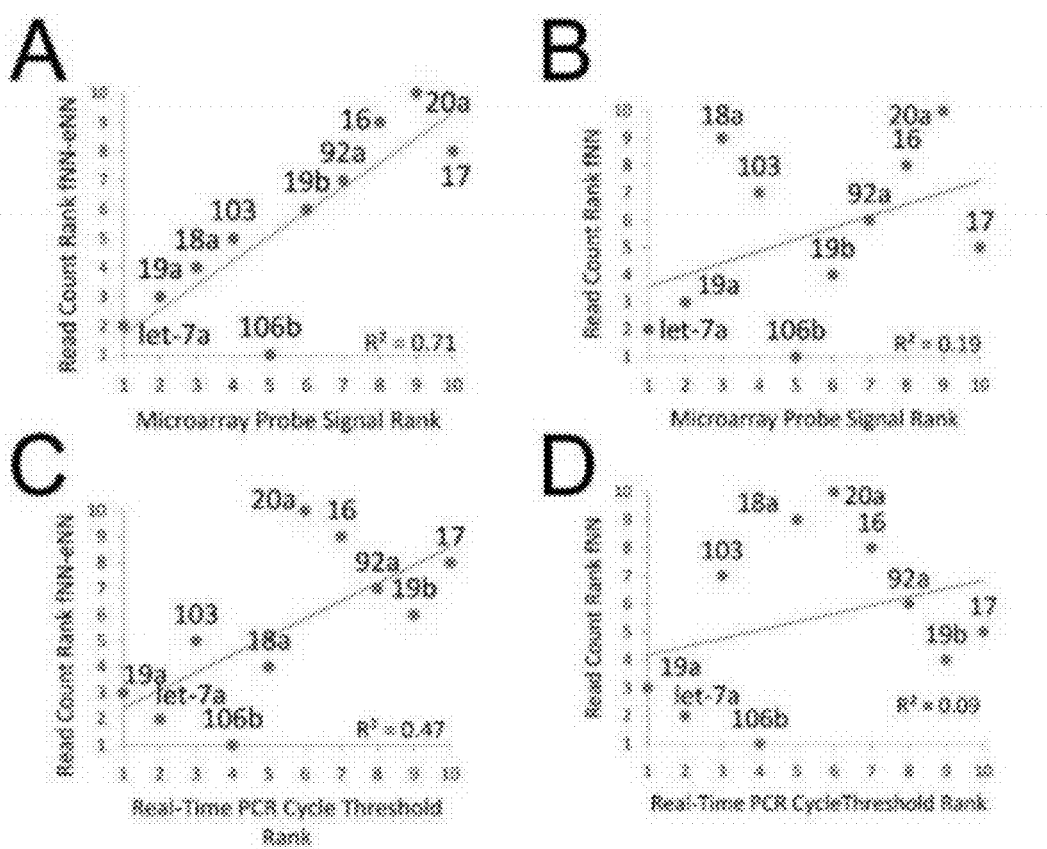
FIG. 9 depicts a comparison of sequencing against microarray (panels A and B) and RT-PCR (panels C and D) for mES (panels A and C) and 293T (panels B and D)

Our proposed strategy, fNN eNN, is one that optimally picks up most sequences, and can help overcome the effect of the biases and increase the efficiency of small RNA sequencing. FIG. 9 depicts a comparison of sequencing against microarray (FIGS. 9A and 9B) and RT-PCR (FIGS. 9C and 9D) for mES (FIGS. 9B and 9D) and 293T (FIGS. 9A and 9C). There were outliers, such as miR-106b, that were only captured by the fNNNN strategy, but overall, there was significant correlation between the fNN eNN strategy and the microarray data (FIG. 9A) and the fNN eNN strategy and the RT-PCR data (FIG. 9C), while the fNN sequencing strategy does not correlate as well to RT-PCR and array data (FIG. 9B and FIG. 9D).

Figure 10:
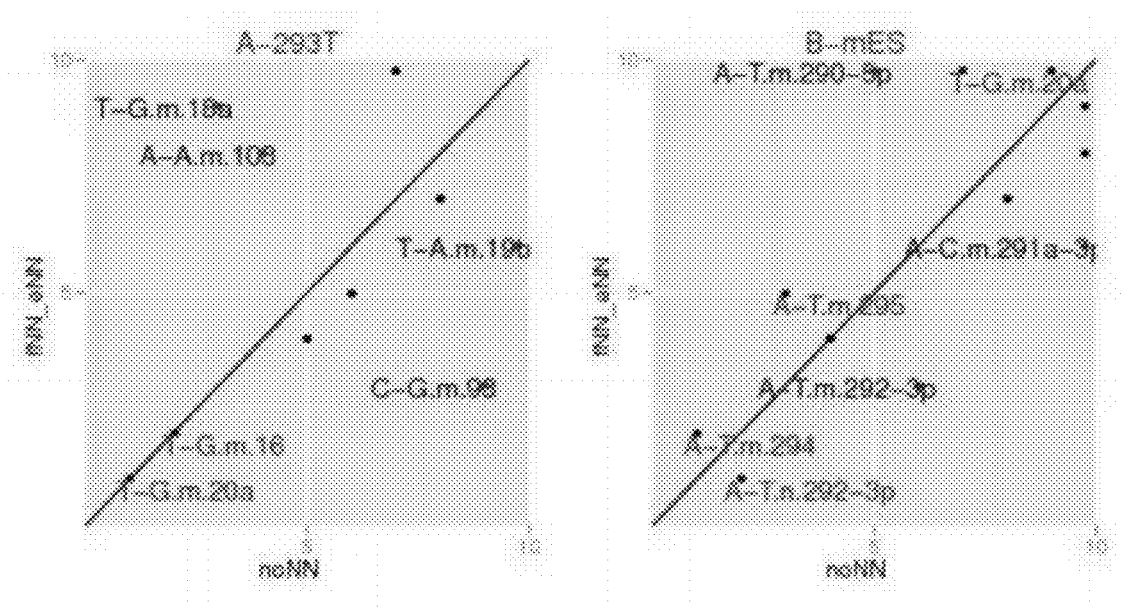
FIG. 10 shows a comparison of rankings between the standard adapters (noNN, ranks along x-axis) versus fNN eNN (ranks along y-axis) for 293T (left panel) and mES samples.

Using the fNN eNN technique, we have identified several miRNAs in mouse embryonic stem cells and human kidney derived 293T cells that are severely underrepresented in the current published profiles based on deep-sequencing. FIG. 10 depicts a comparison of rankings between the standard adapters (noNN, ranks along x-axis) versus fNN eNN (ranks along y-axis) for 293T (left panel) and mES samples (right panel). A point above the diagonal represents a sequence that was over-represented in noNN, while below the diagonal are points that were under-represented in noNN. The hsamiR-18a was over-represented in the noNN case, where it was ranked 3, the array and qPCR data agreed better with the fNN eNN results which ranked it much lower (this skew was also seen in the mES samples, but the ranking in the noNN was 22 while the fNN eNN was much lower (135). In the mES sample, mmu-miR-294 was first and a non-canonical form of mmumir-292-3p was second for noNN. While they switched ranks in the fNN eNN case, the difference is very significant because the abundances of the first and the second ranks were about 2-fold apart, indicating a strong bias. mmu-miR-290-5p was very high at rank 5 in the case of noNN, it was outside the range of the graph in fNN eNN, in accordance with the qPCR data. Thus, in every case in which a difference was detected between noNN and fNN eNN, fNN eNN was more accurate in reflecting the profiles.

Thus, we have established the existence of a pronounced, sequence-dependent bias in the ligation of 5' and 3' sequencing adapters to miRNAs. Our proposed strategy, fNN eNN will be able to overcome the limitations of the bias in the RNA-ligase and make sRNA-seq more representative of the profiles in the underlying samples.

Example 3

Our experiments provide an understanding for the biases observed with sRNA-seq. We have identified and quantified biases in the functioning of the T4-RNA ligases (Rnl1, Rnl2) through deep sequencing, and the large numbers of ligated sequences generated here provide a measure of statistical reliability to our results. "Deep sequencing" is used herein in conformity with the ordinary meaning of the term in the art, i.e., high-throughput sequencing methodology such as the massively parallel sequencing methodologies of lumina and 454.

Reasons for Biases in the Ligase Activity

Bacteria, under viral attack, nick their tRNAs to block translation. The T4-phage uses the ligases to repair the nick. Since the nicks are made at specific sequences in the tRNAs, the ligase structure most likely have evolved sequence-specificity to efficiently repair the nicks.

Profiling Studies

Our studies have important implications for profiling studies ongoing in the fields of genomic profiling of small RNAs, such as studies in cancer and stem cells, that attempt to identify bio-markers for diagnosis and therapies.

Even a small change in the ranking, from say 1 to 2, reflects a big change in numbers. Thus a small change in the profile is a profound change in the underlying numbers, which can have important implications for the kinetics of the reactions mediated by the miRNA.

There are several mES-specific miRNAs. The microRNA, mmu-miR-292-3p, has two forms, a canonical form and a longer non-canonical form with an extra A at the 5' end. This suggests that the two forms have different targets. Thus, it is important to understand their relative abundances as it might have important implications for stem-cell biology. In the normal protocol, with the standard adapters, the canonical form is ranked second, while the non-canonical form is about one-third as abundant (1,305,991 versus 552,573). In the fNN eNN strategy, the two are the highest ranked, with the canonical form ranked first and the non-canonical form ranked second and about two-thirds as abundant (3,085,673 versus 2,356,385). The microarray ranks both as the most abundant miRNAs, but it probably cannot distinguish between the two isoforms.

The Model

The ability of a unified model to predict the outcomes of sample preparations using different adapters suggests that the effects are not stochastic. From the model that we have discussed for the ligation bias, it might appear that a single set of 5' and 3' adapters might suffice, allowing for mathematical corrections to be applied to the profiles that are derived. This is illusory, since, for every adapter, we see at least one transcript that seems to be inefficiently ligated. Applying large corrections can result in excessive noise, reducing the reliability of the corrected results. Thus, in applications where it is critical to establish accurate profiles, using pooled adapters of fNN eNN strategy might be the best approach. We have made a persuasive case for this through our series of experiments.

Explaining the Gel-Shift Experiment

We can derive an equation similar to Equation 2, for the ratios of actual measures values for the members of these pairs. In order to explain the gel-shift experiment, we have to pick eNN data for two miRNAs that have the same 3' terminus as the 19-mer (GA) and the 24-mer (GT), and identical 5' termini. The pair, (TATT-CTGT.m.h-92a, TAGC-TTGA.m.h-21) satisfy the requirements for the ends of the sequences. The ratio of the measured values divided by the ratio of the estimated values of the miRNAs in the sample (using estimates from the fNN eNN case), is the ratio of ligation efficiencies. For the pair, (TATTCTGT. m.h-92a, TAGC-TTGA.m.h-21) the ratios of the ligation efficiencies works out to 0.53, so we would predict that the 19 mer would be twice as efficiently captured as the 24 mer. It is tough to estimate these numbers accurately, as the abundances of the two miRNAs in the pair is not very high.

fNNNN Strategy

The miRNAs, mir-106b and mir-20a are identical at the first 9 nucleotides on the 5' end. Despite this, mir-106b is efficiently captured only in the fNNNN strategy by a few adapters (as we already discussed in FIGS. 2,4), but the fNN strategy does not capture mir-106b very efficiently. In contract, mir-20a is efficiently captured by both the fNNNN and the fNN strategies. This indicates that there might be other factors such as secondary structures that could influence the ligation. It is also of biological interest to identify the distinct roles of the two miRNAs (especially as mir-20a seems to be abundant in many tissues) and if the inefficiencies in capturing mir-106b has led to its role being overlooked.

miRNA Clusters

It is believed that all members of a miRNA cluster (miRNAs that are in close proximity (<1 Kb apart from each other) are processed from a single transcriptional unit, in which case, differential expression patterns within a cluster implies differential regulation. Thus, accurate measurement of the relative numbers for members of a cluster is biologically very relevant. We can extract numbers for two clusters, (miR-106b, miR-93, miR-25) that we label the 106b cluster and (miR-17, miR-18a, miR-19a, mir-92a, mir-19b, miR-20a) that we label the mir17 cluster. Depending on the strategy used, the relative amounts within each cluster are different. For the 106b cluster, the numbers (fold-change) relative to the miR-106b abundance are, noNN (1.0, 4.8, 1.6) and fNN eNN (1.0, 9.4, 1.95), there is a big change in the relative abundance of miR-93. For the mir17 cluster, the numbers (fold-change) relative to the miR-17 abundance are, for noNN (1.0, 1.19, 0.32, 0.70, 0.50, 3.39) and for fNN eNN (1.0, 0.45, 0.26, 0.80, 0.50, 2.30), there is a big change in the relative abundance of miR-18a. Thus, depending on the technique used, we have a different interpretation for the miR-17 abundance.

Abundance of Star Sequences

In microRNAs, the star sequence is usually degraded and not found in the sequencing data, but occasionally, for certain abundant miRNAs, the star sequence is also captured. A question that often arises is how abundant the star sequence is and if it has any function. In the case of miR-17 in 293T cells, we find two star forms, the canonical one (*) and a form with an extra C at the 3' end (*C). The relative numbers of the star forms (*,*C) versus the mature for different techniques are, fNN eNN (0.176, 0.2) and noNN (0.0672, 0.23). The star sequence abundance is strongly dependent on the sequencing method.

piRNA Sequencing piRNAs are small RNAs, 28-32 nt long, that are exclusively expressed in animal gonads. They are involved in transposon control and germline maintenance. Deep sequencing has been used to analyze piRNAs, mainly from Drosophila and mouse. A distinguishing feature of a particular class of piRNAs (primary piRNAs) is the bias for a T at position 1, and a change in this bias is considered an indication for piRNA processing defects. In a particular experiment, small RNA libraries were generated from wild-type and mutant samples using 5' adapters with same ends (TC). The resultant sequence sets showed >80% T-bias. However, generation of biological replicates from additional mutant samples, but now using 5' adapters with different 3' ends, resulted in alarmingly varying T-biases: 73% (for an adapter ending in GA), 69% (TA), and 57% (AA). This indicates that a careless choice of adapters can give rise to erroneous conclusions, even comparisons between libraries generated with the same adapters might come with problems, due to the changes in the small RNAs which might result in different efficiencies of adapter ligation.

Practical Implications

The practical implications of these studies are that:

Profiling by sequencing needs to be done using pools of adapter sequences.

Isomer profiles generated using a single adapter sequence need to be revisited.

Many studies have reported end-modifications of mature sequences, such as, uridylation. The modifications might have been under- (or over-) reported, because of the biases in the activity of the ligases.

The isoforms identified as mature in mirBase are usually the dominant ones, which may reflect the biases of the profiling methods rather than their natural biological enrichment.

Barcoding of samples using adapters, for multiplex sequencing, should be done carefully, taking these results into account. It is expected that by using the methods according to the disclosure, bias in barcoding can be reduced or eliminated.

The studies disclosed herein have established that RNA ligases derived from T4-phage exhibit significant sequence-specificity in their activity. The profiles of small RNAs are strongly dependent on the adapters used for sample preparation. In light of this, the current, popular, sRNA-seq protocols need revision. The disclosure provides that revision in disclosing materials and methods useful in covalently ligating at least 2 nucleotides to the 3' end of a 5' RNA adapter and/or at least 2 nucleotides to the 5' end of a 3' nucleic acid adapter that is either RNA or DNA, with the ligations mediated by an RNA ligase such as T4 RNA Ligase 1, T4 RNA Ligase 2, or truncated T4 RNA Ligase 2. We find that a mix of adapters, with different sequence ends, permits a more accurate estimation of the amounts of individual nucleic acids, such as miRNA sequences and their isoforms.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A mixture of 3' DNA adapters for small RNA characterization comprising:
a plurality of modified adapter sequences that are covalently extended at the 5' ends by addition of at least two random nucleotides, wherein the modified adapter sequences comprise the structure NNe, wherein e is the adaptor sequence, and wherein NN are at least two random nucleotides that have been covalently attached to the 5' end of the adapter sequence;
wherein at least one modified adapter sequence further comprises an activated riboadenylation (rAPP) at the 5' end of the modified adapter sequence, wherein the at least two random nucleotides are internal to the activated riboadenylation (5'rAPP-NNe-3');
wherein the mixture comprises at least sixteen modified adapter sequences for each unique adapter sequence wherein the at least sixteen modified adapter sequences comprise AAe, ACe, AGe, ATe, CAe, CCe, CGe, CTe, GAe, GCe, GGe, GTe, TAe, TCe, TGe, and TTe; and
wherein A is a deoxyadenylate nucleotide; C is a deoxycytidylate nucleotide; G is a deoxyguanylate nucleotide; and T is a thymidylate nucleotide.

2. The mixture of 3' DNA adapters according to claim 1, wherein the 3' adapters are 3' RNA adapters.

3. The mixture of 3' DNA adapters according to claim 1, wherein at least one modified adapter sequence further comprises a restriction endonuclease cleavage site.

4. The mixture of 3' DNA adapters according to claim 1, wherein each adapter sequence of unique sequence is present in about equimolar concentration relative to other adapter sequences of unique sequence in the mixture.

5. The mixture of 3' DNA adapters according to claim 1, wherein at least one modified adapter sequence further comprises a PCR primer binding site.

6. The mixture of 3' DNA adapters according to claim 1, wherein at least one modified adapter sequence comprises: deoxyinosine; deoxy-5-bromouridylate; or deoxyinosine and deoxy-5-bromouridylate.

7. The mixture of 3' DNA adapters according to claim 1, wherein at least one modified adapter sequence further comprises a dideoxy nucleotide at the 3' end of the modified adapter sequence.

8. The mixture of 3' DNA adapters according to claim 1, wherein at least one 3' adapter comprises ribonucleotides.

9. The mixture of 3' DNA adapters according to claim 1, wherein at least one modified adapter sequence further comprises a restriction endonuclease cleavage site.

10. The mixture of 3' DNA adapters according to claim 1, wherein at least one modified adapter sequence further comprises a PCR primer binding site.

11. The mixture of 3' DNA adapters of claim 7, wherein the dideoxy nucleotide is ddC.

12. The mixture of 3' DNA adapters according to claim 1, wherein: at least one modified adapter sequence AAe comprises AAAe, AACe, AAGe, or AATe; at least one modified adapter sequence ACe comprises ACAe, ACCe, ACGe, or ACTe; at least one modified adapter sequence AGe comprises AGAe, AGCe, AGGe, or AGTe; at least one modified adapter sequence ATe, comprises ATAe, ATCe, ATGe, or ATTe; at least one modified adapter sequence CAe comprises CAAe, CACe, CAGe, or CATe; at least one modified adapter sequence CCe comprises CCAe, CCCe, CCGe, or CCTe; at least one modified adapter sequence CGe comprises CGAe, CGCe, CGGe, or CGTe; at least one modified adapter sequence CTe comprises CTAe, CTCe, CTGe, or CTTe; at least one modified adapter sequence GAe comprises GAAe, GACe, GAGe, or GATe; at least one modified adapter sequence GCe comprises GCAe, GCCe, GCGe, or GCTe; at least one modified adapter sequence GGe comprises GGAe, GGCe, GGGe, or GGTe; at least one-modified adapter sequence GTe comprises GTAe, GTCe, GTGe, or GTTe; at least one modified adapter sequence TAe comprises TAAe, TACe, TAGe, or TATe; at least one modified adapter sequence TCe comprises TCAe, TCTe, TCGe, or TCTe; at least one modified adapter sequence TGe comprises TGAe, TGCe, TGGe, or TGTe; or at least one modified adapter sequence TTe comprises TTAe, TTCe, TTGe, or TTTe.

13. The mixture of adapters according to claim 12, wherein the random nucleotides of at least one modified adapter sequence further comprises an additional A, C, G, or T random nucleotide.

14. A mixture of 5' adapters and 3' adapters comprising:
a plurality of 5' modified adapter sequences and a plurality of 3' modified adapter sequences, wherein the 5' modified adapter sequences comprise RNA and the 3' modified adapter sequences comprise DNA and an activated riboadenylation (rAPP) at the 5' end;
wherein each modified adapter sequence comprises an adapter sequence and two random nucleotides, wherein the two random nucleotides are located on the 3' end of the 5' modified adapter sequences and wherein the two random nucleotides are located between the activated adenylation and the adapter sequence of the 3' modified adapter sequences;
wherein for each 5' adapter sequence of unique sequence in the mixture, the mixture comprises sixteen modified adapter sequences, each comprising the unique adapter sequence and one of the sixteen possible combinations of two random nucleotides; and wherein for each 3' adapter sequence of unique sequence in the mixture, the mixture comprises sixteen modified adapter sequences, each comprising the unique adapter sequence and one of the sixteen possible combinations of two random nucleotides.

15. A mixture of 5' adapters and 3' adapters comprising:

a plurality of 5' modified adapter sequences and a plurality of 3' modified adapter sequences, wherein the 5' modified adapter sequences comprise RNA and the 3' modified adapter sequences comprise DNA and an activated riboadenylation (rAPP) at the 5' end;

wherein each modified adapter sequence comprises an adapter sequence and three random nucleotides, wherein the three random nucleotides are located on the 3' end of the 5' modified adapter sequences and wherein the three random nucleotides are located between the activated adenylation and the adapter sequence of the 3' modified adapter sequences;

wherein for each 5' adapter sequence of unique sequence in the mixture, the mixture comprises sixty four modified adapter sequences, each comprising the unique adapter sequence and one of the sixty four possible combinations of three random nucleotides; and wherein for each 3' adapter sequence of unique sequence in the mixture, the mixture comprises sixty four modified adapter sequences, each comprising the unique adapter sequence and one of the sixty four possible combinations of three random nucleotides.

16. A mixture of 5' adapters and 3' adapters comprising:

a plurality of 5' modified adapter sequences and a plurality of 3' modified adapter sequences, wherein the 5' modified adapter sequences comprise RNA and the 3' modified adapter sequences comprise DNA and an activated riboadenylation (rAPP) at the 5' end;

wherein each modified adapter sequence comprises an adapter sequence and four random nucleotides, wherein the four random nucleotides are located on the 3' end of the 5' modified adapter sequences and wherein the four random nucleotides are located between the activated adenylation and the adapter sequence of the 3' modified adapter sequences;

wherein for each 5' adapter sequence of unique sequence in the mixture, the mixture comprises two hundred and fifty six modified adapter sequences, each comprising the unique adapter sequence and one of the two hundred and fifty six possible combinations of four random nucleotides; and wherein for each 3' adapter sequence of unique sequence in the mixture, the mixture comprises two hundred and fifty six modified adapter sequences, each comprising the unique adapter sequence and one of the two hundred and fifty six possible combinations of four random nucleotides.

17. The mixture of 3' DNA adapters according to claim 1, wherein the at least two random nucleotides comprise deoxyguanylate, deoxyadenylate, thymidylate, deoxycytidylate, guanylate, adenylate, uridylate, cytidylate, deoxyinosine monophosphate, inosine monophosphate, deoxy-5-bromouridylate or 5-bromouridylate.

* * * * *

SEQUENCE LISTING

```
<160> NUMBER OF SEQ ID NOS: 29

<210> SEQ ID NO 1
<211> LENGTH: 19
<212> TYPE: RNA
<213> ORGANISM: Artificial Sequence
<220> FEATURE:
<223> OTHER INFORMATION: Synthetic sequence

<400> SEQUENCE: 1
cguacgguuu aaacuucga                                                   19

<210> SEQ ID NO 2
<211> LENGTH: 24
<212> TYPE: RNA
<213> ORGANISM: Artificial Sequence
<220> FEATURE:
<223> OTHER INFORMATION: Synthetic sequence

<400> SEQUENCE: 2
cguacgguuu aaacuucgaa augu                                             24

<210> SEQ ID NO 3
<211> LENGTH: 17
<212> TYPE: DNA
<213> ORGANISM: Artificial Sequence
<220> FEATURE:
<223> OTHER INFORMATION: Synthetic sequence

<400> SEQUENCE: 3
attgatggtg cctacag                                                     17
```

```
<210> SEQ ID NO 4
<211> LENGTH: 41
<212> TYPE: DNA
<213> ORGANISM: Artificial Sequence
<220> FEATURE:
<223> OTHER INFORMATION: Synthetic sequence

<400> SEQUENCE: 4
aatgatacgg cgaccaccga acactctttc cctacacgac g                    41

<210> SEQ ID NO 5
<211> LENGTH: 36
<212> TYPE: DNA
<213> ORGANISM: Artificial Sequence
<220> FEATURE:
<223> OTHER INFORMATION: Synthetic sequence

<400> SEQUENCE: 5
aagcagaaga cggcatacga ttgatggtgc ctacag                          36

<210> SEQ ID NO 6
<211> LENGTH: 32
<212> TYPE: RNA
<213> ORGANISM: Artificial Sequence
<220> FEATURE:
<223> OTHER INFORMATION: Synthetic sequence

<400> SEQUENCE: 6
acacucuuuc ccuacacgac gcucuuccga uc                              32

<210> SEQ ID NO 7
<211> LENGTH: 17
<212> TYPE: DNA
<213> ORGANISM: Artificial Sequence
<220> FEATURE:
<223> OTHER INFORMATION: Synthetic sequence

<400> SEQUENCE: 7
ctgtaggcac catcaat                                               17

<210> SEQ ID NO 8
<211> LENGTH: 34
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (33)..(34)
<223> OTHER INFORMATION: n is a, c, g, or u

<400> SEQUENCE: 8
acacucuuuc ccuacacgac gcucuuccga ucnn                            34

<210> SEQ ID NO 9
<211> LENGTH: 17
<212> TYPE: DNA
<213> ORGANISM: Artificial Sequence
<220> FEATURE:
<223> OTHER INFORMATION: Sythetic sequence

<400> SEQUENCE: 9
ctgtaggcac catcaat                                               17

<210> SEQ ID NO 10
<211> LENGTH: 36
<212> TYPE: RNA
```

```
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (33)..(36)
<223> OTHER INFORMATION: n is a, c, g, or u

<400> SEQUENCE: 10
acacucuuuc ccuacacgac gcucuuccga ucnnnn                           36

<210> SEQ ID NO 11
<211> LENGTH: 17
<212> TYPE: DNA
<213> ORGANISM: Artificial Sequence
<220> FEATURE:
<223> OTHER INFORMATION: Synthetic sequence

<400> SEQUENCE: 11
ctgtaggcac catcaat                                                17

<210> SEQ ID NO 12
<211> LENGTH: 32
<212> TYPE: RNA
<213> ORGANISM: Artificial Sequence
<220> FEATURE:
<223> OTHER INFORMATION: Synthetic sequence

<400> SEQUENCE: 12
acacucuuuc ccuacacgac gcucuuccga uc                               32

<210> SEQ ID NO 13
<211> LENGTH: 19
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(2)
<223> OTHER INFORMATION: n is a, c, g, or t

<400> SEQUENCE: 13
nnctgtaggc accatcaat                                              19

<210> SEQ ID NO 14
<211> LENGTH: 34
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (33)..(34)
<223> OTHER INFORMATION: n is a, c, g, or u

<400> SEQUENCE: 14
acacucuuuc ccuacacgac gcucuuccga ucnn                             34

<210> SEQ ID NO 15
<211> LENGTH: 19
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(2)
<223> OTHER INFORMATION: n is a, c, g, or t
```

-continued

```
<400> SEQUENCE: 15
nnctgtaggc accatcaat                                                   19

<210> SEQ ID NO 16
<211> LENGTH: 36
<212> TYPE: DNA
<213> ORGANISM: Artificial Sequence
<220> FEATURE:
<223> OTHER INFORMATION: Synthetic sequence

<400> SEQUENCE: 16
acacucuuuc ccuacacgac gcucuuccga ucctag                                36

<210> SEQ ID NO 17
<211> LENGTH: 36
<212> TYPE: DNA
<213> ORGANISM: Artificial Sequence
<220> FEATURE:
<223> OTHER INFORMATION: Synthetic sequence

<400> SEQUENCE: 17
acacucuuuc ccuacacgac gcucuuccga ucgagt                                36

<210> SEQ ID NO 18
<211> LENGTH: 36
<212> TYPE: DNA
<213> ORGANISM: Artificial Sequence
<220> FEATURE:
<223> OTHER INFORMATION: Synthetic sequence

<400> SEQUENCE: 18
acacucuuuc ccuacacgac gcucuuccga ucccaa                                36

<210> SEQ ID NO 19
<211> LENGTH: 36
<212> TYPE: DNA
<213> ORGANISM: Artificial Sequence
<220> FEATURE:
<223> OTHER INFORMATION: Synthetic sequence

<400> SEQUENCE: 19
acacucuuuc ccuacacgac gcucuuccga ucagca                                36

<210> SEQ ID NO 20
<211> LENGTH: 36
<212> TYPE: DNA
<213> ORGANISM: Artificial Sequence
<220> FEATURE:
<223> OTHER INFORMATION: Synthetic sequence

<400> SEQUENCE: 20
acacucuuuc ccuacacgac gcucuuccga ucaacc                                36

<210> SEQ ID NO 21
<211> LENGTH: 36
<212> TYPE: DNA
<213> ORGANISM: Artificial Sequence
<220> FEATURE:
<223> OTHER INFORMATION: Synthetic sequence

<400> SEQUENCE: 21
acacucuuuc ccuacacgac gcucuuccga ucaagg                                36

<210> SEQ ID NO 22
```

```
<211> LENGTH: 36
<212> TYPE: DNA
<213> ORGANISM: Artificial Sequence
<220> FEATURE:
<223> OTHER INFORMATION: Synthetic sequence

<400> SEQUENCE: 22
acacucuuuc ccuacacgac gcucuuccga uctgac                                 36

<210> SEQ ID NO 23
<211> LENGTH: 36
<212> TYPE: DNA
<213> ORGANISM: Artificial Sequence
<220> FEATURE:
<223> OTHER INFORMATION: Synthetic sequence

<400> SEQUENCE: 23
acacucuuuc ccuacacgac gcucuuccga uccgtc                                 36

<210> SEQ ID NO 24
<211> LENGTH: 36
<212> TYPE: DNA
<213> ORGANISM: Artificial Sequence
<220> FEATURE:
<223> OTHER INFORMATION: Synthetic sequence

<400> SEQUENCE: 24
acacucuuuc ccuacacgac gcucuuccga ucgctt                                 36

<210> SEQ ID NO 25
<211> LENGTH: 36
<212> TYPE: DNA
<213> ORGANISM: Artificial Sequence
<220> FEATURE:
<223> OTHER INFORMATION: Synthetic sequence

<400> SEQUENCE: 25
acacucuuuc ccuacacgac gcucuuccga ucgtat                                 36

<210> SEQ ID NO 26
<211> LENGTH: 36
<212> TYPE: DNA
<213> ORGANISM: Artificial Sequence
<220> FEATURE:
<223> OTHER INFORMATION: Synthetic sequence

<400> SEQUENCE: 26
acacucuuuc ccuacacgac gcucuuccga ucggaa                                 36

<210> SEQ ID NO 27
<211> LENGTH: 36
<212> TYPE: DNA
<213> ORGANISM: Artificial Sequence
<220> FEATURE:
<223> OTHER INFORMATION: Synthetic sequence

<400> SEQUENCE: 27
acacucuuuc ccuacacgac gcucuuccga uctgtg                                 36

<210> SEQ ID NO 28
<211> LENGTH: 17
<212> TYPE: DNA
<213> ORGANISM: Artificial Sequence
<220> FEATURE:
<223> OTHER INFORMATION: Synthetic sequence

<400> SEQUENCE: 28
```

```
ctgtaggcac catcaat                                                     17

<210> SEQ ID NO 29
<211> LENGTH: 19
<212> TYPE: RNA
<213> ORGANISM: Artificial Sequence
<220> FEATURE:
<223> OTHER INFORMATION: Synthetic sequence

<400> SEQUENCE: 29
cguacgguuu aaacuucga                                                   19
```